United States Patent
Durkin et al.

(10) Patent No.: US 8,301,216 B2
(45) Date of Patent: *Oct. 30, 2012

(54) METHOD AND APPARATUS FOR QUANTIFICATION OF OPTICAL PROPERTIES OF SUPERFICIAL VOLUMES USING SMALL SOURCE-TO-DETECTOR SEPARATIONS

(75) Inventors: Anthony J. Durkin, Irvine, CA (US); Sheng-hao Tseng, Plainsboro, NJ (US)

(73) Assignee: The Regents of the University of California, Oakland, CA (US)

( * ) Notice: Subject to any disclaimer, the term of this patent is extended or adjusted under 35 U.S.C. 154(b) by 426 days.

This patent is subject to a terminal disclaimer.

(21) Appl. No.: 12/643,789

(22) Filed: Dec. 21, 2009

(65) Prior Publication Data

US 2010/0160754 A1    Jun. 24, 2010

Related U.S. Application Data

(60) Provisional application No. 61/140,323, filed on Dec. 23, 2008.

(51) Int. Cl.
*A61B 5/00* (2006.01)

(52) U.S. Cl. ........................ 600/342

(58) Field of Classification Search .............. 600/306, 600/342
See application file for complete search history.

(56) References Cited

U.S. PATENT DOCUMENTS

| | | | | |
|---|---|---|---|---|
| 4,790,295 | A * | 12/1988 | Tashiro ........................ 600/176 |
| 5,640,247 | A * | 6/1997 | Tsuchiya et al. .............. 356/446 |
| 6,678,541 | B1 * | 1/2004 | Durkin et al. ................. 600/310 |
| 7,139,068 | B2 * | 11/2006 | Jung et al. ...................... 356/73 |
| 7,304,724 | B2 * | 12/2007 | Durkin et al. ................... 356/73 |
| 2003/0023172 | A1 * | 1/2003 | Tromberg et al. ............. 600/476 |
| 2004/0092802 | A1 * | 5/2004 | Cane et al. ..................... 600/306 |
| 2007/0201788 | A1 * | 8/2007 | Liu et al. ......................... 385/12 |
| 2008/0194928 | A1 * | 8/2008 | Bandic et al. ................. 600/306 |

* cited by examiner

*Primary Examiner* — Rodney Fuller
(74) *Attorney, Agent, or Firm* — Marcus C. Dawes; Daniel L. Dawes

(57) ABSTRACT

A probe for obtaining quantitative optical properties and chromophore concentrations of tissue components in tissue in-vivo at superficial depths and at source-detector separations of 5 mm or less includes a source fiber providing light to expose the tissue, a diffuser layer into which light from the source fiber is directed and then from the diffuser layer to and/or into the tissue, and a detector fiber arranged relative to the diffuser layer for detecting backscattered and/or reflected light returned from the tissue without transmission through the diffuser layer.

19 Claims, 9 Drawing Sheets

… … …

METHOD AND APPARATUS FOR QUANTIFICATION OF OPTICAL PROPERTIES OF SUPERFICIAL VOLUMES USING SMALL SOURCE-TO-DETECTOR SEPARATIONS

RELATED APPLICATIONS

The present application is related to U.S. Provisional Patent Application Ser. No. 61/140,323, filed on Dec. 23, 2008, which is incorporated herein by reference and to which priority is claimed pursuant to 35 USC 119.

STATEMENT OF GOVERNMENT SUPPORT

This invention was made with Government support under Grant No. RR001192, awarded by the National Institutes of Health. The Government has certain rights in this invention.

BACKGROUND OF THE INVENTION

The invention relates to the field of methods and probe designs for obtaining quantitative optical properties and chromophore concentrations of tissue components in-vivo at superficial depths and "short" source-detector separations.

The absorption coefficient $\mu_a$, the scattering coefficient $\mu_s'$, and chromophore concentrations of skin are fundamental properties of tissue that can provide essential information for many aesthetic, therapeutic, and diagnostic applications such as monitoring of skin blood oxygenation, melanin concentration, detection of cancer with fluorescence, laser surgery, and photodynamic therapy. Many researchers have quantified the optical properties of skin tissue and most of them used ex-vivo skin samples and integrating sphere techniques.

Although the integrating sphere based techniques can be used to investigate ex vivo optical properties of epidermis, dermis, and subcutaneous tissue, the need to take biopsies from subjects limits their applicability in the clinic. Furthermore, once tissue has been excised, it is no longer part of the living organism; oxy and dexoyhemoglobin concentrations begin to diverge from physiologic quantities and if not carefully handled, the hydration of the tissue begins to change.

Photon diffusion theory may be employed to determine optical properties of in vivo samples at source-detector separation longer than five mean-free-paths, where mean-free-path is defined as $1/(\mu_a+\mu_s')$. It has been proven to be a not adequate model because boundary conditions and the assumption of multiple scattering in a turbid medium cannot be satisfied. In order to limit interrogation to superficial tissue volumes, such as skin, source-detector separations shorter than five mean-free-paths are more favorable. In-vivo techniques which are capable of measuring optical properties of skin do exist, but have some important limitations. For example, optical properties have been measured of in-vivo skin using visible reflectance spectroscopy with a multi-layer skin model and a genetic optimization algorithm. A multi-layer skin model and a number of fitting parameters, such as layer thickness, chromophores, and scattering properties for each layer, and their corresponding ranges must be chosen carefully in advance to avoid nonuniqueness in the solution space. Some have proposed a model to extract optical properties from diffuse reflectance spectra collected from human skin in-vivo. This technique requires that all of the chromophores contributing to the measured signals are known in advance and the reduced scattering coefficient has a linear relation to the wavelength in order to separate absorption and reduced scattering coefficients from measured reflectance. For the case where all constituent chromophores cannot be determined, the absorption spectra cannot be recovered. In addition, for the case where the reduced scattering coefficient does not have a linear dependence on wavelength, the empirical mathematical model will not recover tissue optical properties properly.

Probes for use in free space or for quantitative measurements of chromophores in tissues that can be reached by an endoscope or similar instrument in which the source and detector are in relatively close proximity with one another has been a significant challenge for quantitative optical methods.

Diffuse optical spectroscopy using frequency modulated light has been employed for years to quantify in-vivo tissue constituents and optical properties. Diffusion approximation to the equation of radiative transport provides a modeling framework for this approach, and gives an accurate description of light propagation in thick tissues as long as detected photons have undergone at least 10 scattering events before they reach the detector. Similarly, this approach is constrained to situations in which the reduced scattering coefficient, $\mu_s'$ is greater (by an order of magnitude) than the absorption coefficient. In practical terms, this limits the technique to source-detector separations of about 5 mm (depths of about 2.5 mm), wavelengths between 650-1000 nm and modulation frequencies between 50 and 600 MHz.

As source detector separation is reduced to distances smaller than 10 mm, the validity of diffusion approximation is reduced along with ability to accurately recover optical properties and chromophore concentrations. As this distance becomes smaller, the average number of scattering events that photons experience before detection is also reduced. Similarly as one moves to more highly absorbing spectral domains (shorter wavelengths than 650 nm and longer wavelengths than 1000 nm), a reduction in source-detector separation is necessary in order to collect light with reasonable signal to noise ratio. In each of these cases, a simple application of diffusion approximation based modeling will yield inaccurate tissue optical properties and chromophore concentrations.

The problem of quantifying superficial chromophores and optical properties has been solved in the past primarily using multivariate calibration techniques such as the method of Partial Least Squares (PLS). In such an approach, signals are acquired from a set of samples that are representative of the sample of interest. The concentration of the analyte of interest must be known for each sample included in the calibration. By sampling many "reference" samples, an empirical model relating spectral shapes to analyte concentration can be developed. The problem with this approach is that the calibration samples have to be very similar to the target (unknown) sample set of interest. In addition, there has to be a way of recovering the true concentration of the analyte of interest in each of those samples, using a separate method, so that a correlative model can be developed. Note that initial experiments have involved a highly diffusing layer that is, for all practical purposes, infinite in the X-Y dimensions. Clearly this is impractical when thinking in terms of a probe for interrogating, for example, oral tissues.

BRIEF SUMMARY OF THE INVENTION

The illustrated embodiments of the invention are directed to a probe for obtaining quantitative optical properties and chromophore concentrations of tissue components in tissue in-vivo at superficial depths and at source-detector separations of 5 mm or less, and typically with source-detector separations of 3 mm or less. One embodiment of the invention comprises a source fiber providing light to expose the tissue, a diffuser layer into which light from the source fiber is directed and then from the diffuser layer to and/or into the tissue, and a detector fiber arranged relative to the diffuser layer for detecting backscattered and/or reflected light returned from the tissue without transmission through the diffuser layer.

The illustrated embodiment of the probe further comprises a processor circuit including a spectrometer optically coupled to the detector fiber for analyzing the backscattered and/or reflected light from the tissue to determine the quantitative optical properties and chromophore concentrations of tissue components.

The probe in another embodiment may further comprise a light source optically coupled to the source fiber, which light source is a laser or halogen light. The laser may be a swept laser so that a range of wavelength are measured in any given session.

The detector fiber is disposed through the diffuser layer or otherwise arranged so that the detected light does not propagate through the diffuser layer. In the illustrated embodiment the diffuser layer is composed of Spectralon®, but may include any material which has a low absorption coefficient such as one equal to or less than approximately $\mu_a=10^{-6}$/mm. The diffuser also has a reduced scattering coefficient equal or greater than $\mu_s'=35$/mm.

The probe in some embodiments may be configured into an endoscope with a distal end and a lateral boundary at the distal end. The probe is provided at or near the distal end of the endoscope as an endoscopic window. The diffuser layer has a minimum width greater than 1 mm so that the lateral boundary of the endoscope does not substantially affect probe measurements. For example, the minimum width of the diffuser layer may be 6.5 mm or greater and the diffuser layer provided in the shape of a disk.

The illustrated embodiments of the probe may further comprise a plurality of source fibers, where each source fiber has a different distance from the detector fiber so that each source-detector fiber pair provides a depth sectioning measurement sensitive to a corresponding different volume of tissue. Similarly, the probe may further comprise a plurality of detector fibers, where each detector fiber having a different distance from the source fiber so that each source-detector fiber pair provides a depth sectioning measurement sensitive to a corresponding different volume of tissue. In one embodiment the plurality of source and detector fibers are each spaced from each other, and in another embodiment the plurality of source and detector fibers are each adjacent to each other. The probe may include at least one spacer fiber and the source, detector and spacer fibers are then bundled together to form an adjacent collection of fibers. For example, in one embodiment the probe further comprises a plurality of spacer fibers and a plurality of detector fibers arranged and configured with the source fiber to form a compact bundler of fibers with a plurality of spacings between the source fiber and each of the plurality of detector fibers, so that each source-detector fiber pair provides a depth sectioning measurement sensitive to a corresponding different volume of tissue.

In one illustrated embodiment the source and detector fibers have a distal planar area and the diffuser layer has a side boundary and a planar area of the same order of magnitude at the distal planar area of the source and detector fibers themselves and the side boundary of diffuser layer is provided with a reflective material.

In another embodiment the diffuser layer, source and detector fibers are characterized by a maximum width having a magnitude less than a hollow core needle employed for breast cancer biopsy or for transurethral delivery to the prostate or bladder.

The scope of the invention also expressly includes a method for performing measurements of the optical properties of tissue using any one of the above embodiments of the probe.

For example, in one embodiment the method is used for self-calibrating a tissue probe having a plurality of source-detector pairs with a corresponding plurality of source-detector separation distances in which probe light from the source corresponding to each source-detector pair is transmitted through a diffuser layer, and in which probe each detector corresponding to each source-detector pair receives light from the tissue without transmission through the diffuser layer. The method comprises the steps of selecting and measuring one of the plurality of source-detector pairs as a reference reflectance measurement, measuring and normalizing the reflectances from the remaining other ones of the plurality of source-detector pairs, and generating a corresponding plurality of normalized reflectance versus source-detector separation curves to fit the measurements obtained from the plurality of source-detector pairs included in the probe.

Still further, the scope of the invention also expressly includes a data output or report of the optical properties of tissue using any one of the above embodiments of the probe.

Further, the scope of the invention also expressly includes instructions stored on a tangible medium for controlling a computer or processing circuit to measure the optical properties of tissue using any one of the above embodiments of the probe.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 1a is a diagram of a semi-infinite measurement geometry, and FIG. 1b is a diagram of a modified two-layer geometry according to the illustrated embodiments. The top diffuser layer with optical properties $\mu_{a1}, \mu_{s\,1}$ is a high scattering and low absorption medium, in the illustration, undiluted 10% Liposyn.

Figure 1A:
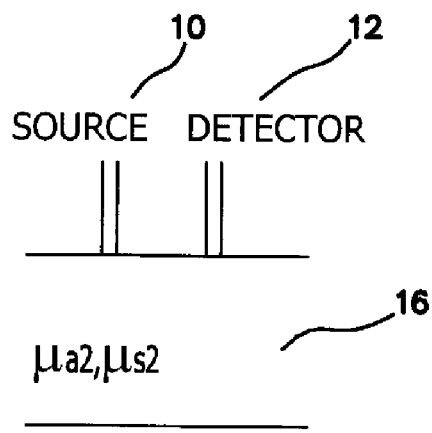
FIGS. 1a and 1b are schematic diagrams of a tissue phantom with optical properties $\mu_{a2}, \mu_{s\,2}$ which represents the skin or tissue of a patient being examined by the apparatus and according to the method of the illustrated embodiments.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE ILLUSTRATED EMBODIMENTS

The probe of the illustrated embodiments is amenable to use in free space or for quantitative measurements of chromophores in tissues that can be reached by an endoscope or similar instrument. We present a method to reduce source-detector separation while maintaining the validity of the diffusion approximation, which employs a high scattering, low absorption layer ($\mu_s'$=9 mm$^{-1}$ and $\mu_a$=0.0015 mm$^{-1}$ at 661 nm) placed on the surface of the tissue under investigation. This effectively increases the photon path length and allows the source-detector separation to be made arbitrarily small. In order to demonstrate feasibility, we have carried out frequency domain measurements at several wavelengths to recover the optical properties of tissue phantoms, using a two-layer model for which the optical properties and thickness of the upper, highly scattering layer are known.

In a sense, the approach of the illustrated embodiments of the invention "force" diffusive light propagation on the sample of interest. As a result, what is realized is an expanded wavelength range. In the illustrated embodiments we demonstrate this with data over the range 500-1000 nm. Further, what results is a design for an endoscope compatible probe. Using a Monte Carlo simulation we demonstrate the plausibility and design aspects of the illustrated embodiments. A further advantage is a new depth sectioning capability by using more than a single source-detector pair to provide depth sectioning with each source detector pair sensitive to different volumes of tissue. A yet another advantage is a self-calibrating probe from the incorporation of multiple source-detector pairs, which allows us to circumvent the need for, or at least reduce dependence on, an external calibration phantom as is currently used for hand-held SSFDPM measurements. This is a significant advance insofar as it makes the process of collecting meaningful data from a widely varying sample set in terms of optical properties such as that one might encounter when doing skin studies using subjects of various skin pigmentations, e.g. Caucasian, Asian, African.

Tissue depths of interest for quantitative characterization of epithelial malignant transformation range from a few tens of microns to a few hundreds of microns. In order to improve our ability to interrogate tissues at these superficial thicknesses, we have developed a method for quantification of superficial optical properties and chromophore concentrations in which we employ a two-layer model shown diagrammatically in FIG. 1b of light propagation in concert with a probe geometry having a high scattering layer with known optical properties. Using this approach the errors of recovered $\mu_a$ and $\mu_s'$ are small (~10%) and is robust to large variations in the magnitude of the initial guess in order to recover optical properties.

Similarly, tissue depths for determining interstitial tissue glucose concentration/distribution range from a few tens of microns to a few hundreds of microns depending on body site probed. If delivered intravascularly, e.g. via a catheter, tissue depths of interest for characterization of vulnerable plaque range from a few tens of microns to a few hundreds of microns. The illustrated embodiments have the capacity to detect inflammatory changes in addition to subsurface pools of lipid which seem to characterize this pathology.

The general context of the measurement is diagrammatically depicted in FIG. 1a where a source of light or probing energy 10 (hereinafter referenced as "light") is directed onto or near a tissue sample or site 16 characterized by the optical parameters of an absorption coefficient, $\mu_{a2}$, and a reduced scattering coefficient, $\mu'_{s2}$. The reflected and/or backscattered light from sample 16 is received as returned light to a proximate detector 12 placed onto or near the tissue sample or site 16. The light delivered by source 10 and received by detector 12 are typically delivered and received through fiber optics. Hence, the terms, "source" or "detector", will be used in this specification to reference either the corresponding fiber optic or the actual source or detector respectively or both.

Figure 1B:
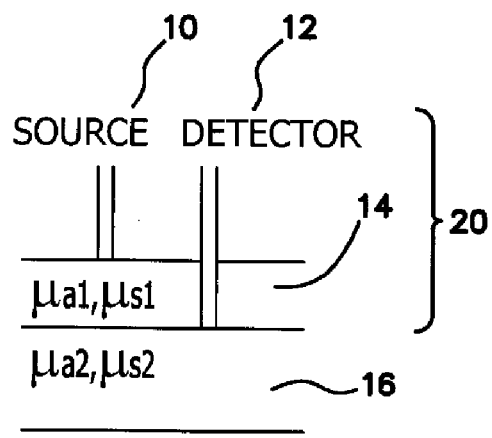

FIG. 1b diagrammatically shows an embodiment of the invention wherein a layer 14 of diffusing material, which is similar in X-Y dimensions to the optically active transmission and receiving windows of the optic fibers of source 10 and detector 12 themselves, is placed between source 10 and sample 16. Detector 12 remains on or near sample 16 and is disposed through or next to layer 14. The arrangement of FIG. 1b also achieves a similar effect in a second embodiment when the side or peripheral boundary of the layer 14 is coated with reflective material 18 as diagrammatically depicted in FIG. 2. Note that the source fiber 10 and detection fiber 12 may be adjacent or near to each other, the fibers may even be touching, permitting the use of the probe in endoscopic applications. Similarly, this design may be made small enough in diameter to be used inside of a hollow core needle, as is employed for breast cancer biopsy. It can also potentially be delivered to prostate or bladder in transurethral fashion.

The illustrated design enables the use of diffusion based modeling techniques for source-detector separations in which diffusion based descriptions of light propagation are typically not valid. This illustrated method does not require the development of a representative, physiologically relevant "training set" of calibration samples and the related analyte concentrations. This previously-used multivariate approach has been one of the sticking points in advance of probes in noninvasive blood glucose technology. It is difficult, time consuming and costly to develop an empirical model based on multivariate approaches that are stable for any individual for any reasonable period of time e.g. weeks. In the illustrated embodiments we have been able to reduce source-detector separation to less than 2.5 mm and quantitatively correctly deduce optical properties in artificial tissue phantoms. This source-detector regime is highly relevant to the development of optical technology for applications that focus on the use of near infrared (650-1000 nm) to probe superficial phenomena, including, for example, spectroscopic characterization of dysplastic oral tissue and skin cancer. However, it must be understood that the wavelength range over which the apparatus and method of the invention may be used is not limited to that shown and described in the illustrated embodiments. Virtually, any wavelength range capable of returning a useful reflected and/or backscatter signal from tissue or samples may be employed according to the spirit and scope of the invention.

We discussed above the design of a diffusing probe 20 that employs a standard two-layer diffusion model to recover the optical properties of turbid samples. This particular probe 20 had a source-detector separation of 2.5 mm and performance was validated with Monte Carlo simulations and homogeneous phantom experiments. The discussion which follows characterizes the performance of this method in the context of two-layer phantoms that mimic the optical properties of human skin. We analyze the accuracy of the recovered top layer optical properties and their dependences on the thickness of the top layer of two-layer phantoms. Our results demonstrate that the optical properties of the top layer can be accurately determined with a 1.6 mm source-detector separation diffusing probe when this layer thickness is as thin as 1 mm. Monte Carlo simulations illustrate that the interrogation depth can be further decreased by shortening the source-detector separation.

Consider now how to estimate the diffusing probe's interrogation depth and its ability to extract accurate optical properties from the top layer of a two-layer tissue phantom. We fabricated two-layer phantoms that consist of top layers of various thicknesses above much thicker substrates. The optical properties of top layers and substrates are similar to those of the epidermis-dermis and subcutaneous fat layer, respectively. By carefully characterizing the two-layer phantoms, we estimate the diffusing probe's sampling depth when it is employed to measure human skin, and thereby determine its applicability to quantify optical properties of in-vivo epidermis-dermis. In addition, we employed Monte Carlo simulations as a qualitative tool to analyze the dependence of interrogation depths on source-detector separations of the diffusing probe in support of our experimental observations.

Figure 6:
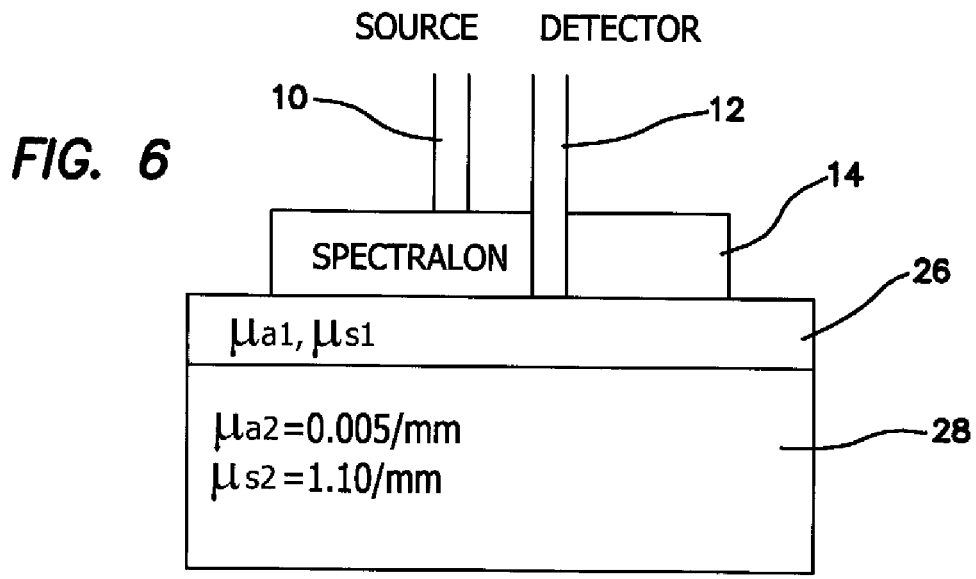
FIG. 6 is a diagram of a two-layer model of tissue according to the illustrated embodiments.

The frequency-domain photon migration instrument used to conduct our DOS measurements conventional and is shown in U.S. Pat. No. 7,428,434 entitled "Quantitative broadband absorption and scattering spectroscopy in turbid media by combined frequency-domain and steady state methodologies", incorporated herein by reference. A single laser diode at 785 nm was swept across a frequency range from 50 MHz to 300 MHz in 90 equal steps. Using multiple modulation frequencies enhances the robustness of the recovery of optical properties. The diffusing probe geometry, illustrated in FIG. 6, is comprised of two optical fibers 10 and 12 (3M, core diameter 600 μm, N.A.=0.37) for delivering and collecting photons, and a highly scattering layer 14 (Spectralon® Slab, Labsphere) to diffuse photons from the source fiber 10. A modified two-layer, diffusion-based model is employed to deduce the sample optical properties from measured phase delay and amplitude demodulation.

We designed our two-layer phantoms according to Simpson's ex-vivo measurement results as shown in C. R. Simpson, M. Kohl, M. Essenpreis, and M. Cope, "Near-infrared optical properties of ex-vivo human skin and subcutaneous tissues measured using the Monte Carlo inversion technique," *Phys. Med. Biol.*, vol. 43, no. 9, pp. 2465-2478, 1998. The optical properties of the top layers 26, 28 are actually averages of epidermis and dermis layers. Ten two-layer and three homogeneous silicone phantoms were made by mixing polydimethylsiloxane (Eager Plastics, IL), catalyst, Titanium dioxide (scatterer), and India ink (absorber) in disposable polystyrene beakers. Ten "bulk" substrates having a thickness of larger than 50 mm were poured at the same time to ensure that all of them have the same optical properties. The substrates were designed to have optical properties similar to those of the subcutaneous fat of skin. Two sets of "top-layer" phantoms, whose optical properties differ from those of the substrate, were then prepared. We designed the optical properties of the two sets of the top-layer phantoms to mimic those of light and dark skin epidermis-dermis. Once the bulk substrate material had cured, the top layers of different thicknesses were poured and allowed to cure. This resulted in five different thicknesses, ranging from about 1 to 8 mm, for each set of top-layer material 26, 28. The absorption coefficient of dark skin phantoms is 200% higher than that of light skin phantoms at the wavelength of 785 nm. Though we have done our best to make the reduced scattering coefficients of light and dark skin phantoms similar, there is a 10% difference. A single bulk substrate was left without a top layer as a control homogeneous phantom. In addition, a 50-mm-thick control homogeneous phantom of each top-layer material was left alone to cure in the absence of an underlying substrate.

Measurements were carried out using two diffusing probes 20 having source-detector separations of 1.6 mm and 3 mm. This allowed us to investigate the influence of source-detector separation on the probing depth of the diffusing probe. The source-detector separation of 1.6 mm is the shortest distance we can achieve with our current fabrication setup, but the distance can be further shortened by using fibers with smaller diameters. Spectralon® slabs 14 having a thickness of 1.5 mm and a diameter of 10 mm were employed for both probes 20.

FIGS. 7a-7d illustrate the recovered or measured absorption and reduced scattering coefficients versus top-layer thickness for the two sets of phantoms. Each symbol in the plot represents the average of three measurements, and deviations are all within 0.1%. Optical properties of samples having a 50-mm-thick top layer are actually results from measurements performed on the control phantoms. We take these results as the benchmark optical properties. Measurement results of the three control homogeneous phantoms are indicated in Table I.

TABLE I

OPTICAL PROPERTIES OF BULK SUBSTRATE
AND TWO BULK TOP-LAYER MATERIALS
AT THE WAVELENGTH OF 785 nm

| | substrate | Low $\mu_a$ top layer | High $\mu_a$ top layer |
|---|---|---|---|
| $\mu_a$ (1/mm) | 0.005 | 0.031 | 0.097 |
| $\mu_s'$ (1/mm) | 1.10 | 2.14 | 1.87 |

From FIGS. 7a-7d, when the top layer is thicker than 2 mm, deviations of absorption coefficient and reduced scattering coefficient from benchmark values for both source-detector separations are within 5% and 1% for light skin and dark skin phantoms, respectively. For the probe 20 with a source-detector separation of 3 mm, as the top-layer thickness decreases to 1 mm, the deviations of recovered from benchmark increase to 27% and 2% for light skin and dark skin phantom sets, respectively. The deviations of recovered from benchmark increase to 32% and 28% for light skin and dark skin phantom sets, respectively. On the other hand, employing the diffusing probe 20 with a source-detector separation of 1.6 mm produced improved results in this region. The deviations of recovered from benchmark increase only to 15% and 2% for light skin and dark skin phantom sets, respectively. The deviations of recovered from benchmark' increase to 12% and 4% for light skin and dark skin phantom sets, respectively.

Our measurement results suggest that deviations of recovered optical properties from benchmark values decrease as the source-detector separation becomes smaller. Decreasing the source-detector separation reduces the influence from the underlying substrate and ultimately increases the accuracy of the recovered optical properties. It is well known that source-detector separation is proportional to the interrogation depth for a DOS probe that has a source and detector in direct contact with samples. We speculate that the interrogation depth of a diffusing probe, such as ours, that has a different source-detector arrangement from a conventional DOS probe, is also proportional to the source-detector separation.

To investigate this, we performed Monte Carlo simulations to estimate the interrogation depth of the diffusing probe. The Monte Carlo code we used was developed from Wang et al.,'s general multilayer, three-dimensional, weighted photon Monte Carlo code. Our code employs a Henyey-Greenstein phase function and uses an anisotropy factor of 0.8 to reduce simulation time because using an anisotropy factor between 0.8 and 1 does not significantly influence the reflectance when is constant. The calculation of the interrogation depth of each simulation can be substantiated in the following manner. Construct a discrete probability density function (pdf), where is the final weight of a detected photon packet and is the number of photon packets launched, then. Using this pdf, the average interrogation depth of a simulation can be estimated as, where is the maximum penetration depth of a detected photon packet. The average of the maximum interrogation depths of a simulation provides a measure of the average depth photons would travel in a homogeneous sample. We designed the simulated sample to be homogeneous with optical properties n=1.43, $\mu_a$=0.33/mm, and $\mu_s'$=2/mm for simulating the light skin, and n=1.43, $\mu_a$=0.09/mm, and $\mu_s'$=1.8/mm for simulating the dark skin. The lateral extension and the thickness of the sample are set as $1\times10^8$ mm. The Spectralon® layer 14 is 1.5 mm thick and has a diameter of 10 mm. Fresnel refraction introduced by index mismatch at the boundaries is taken into account. The optical properties of the Spectralon® are n=1.35, $\mu_a$=1×10$^{-6}$/mm, and $\mu_s'$=35/mm. Source-detector separations used in the Monte Carlo simulations were 1, 2, 3, and 4 mm.

Figure 8:
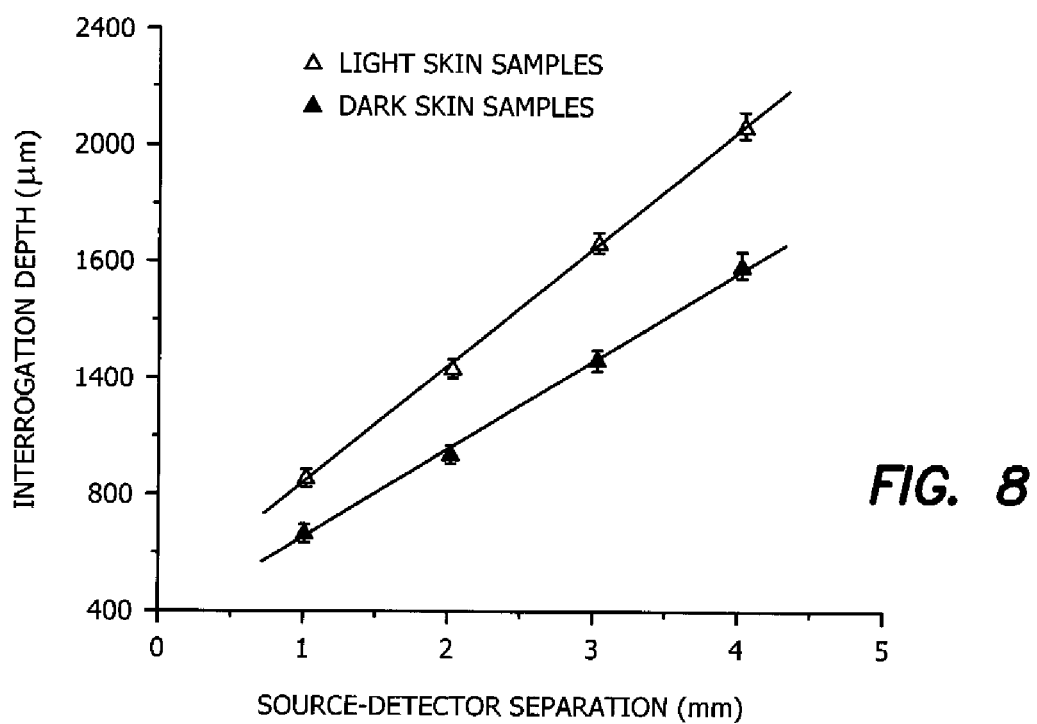
FIG. 8 is a graph of interrogation depth versus diffusing probe's source-detector separation determined from Monte Carlo simulations. Samples have homogeneous semi-infinite geometry. Solid triangles and open triangles represent the interrogation depths of the probe-measuring samples having optical properties of light skin and dark skin, respectively.
Figure 7A:
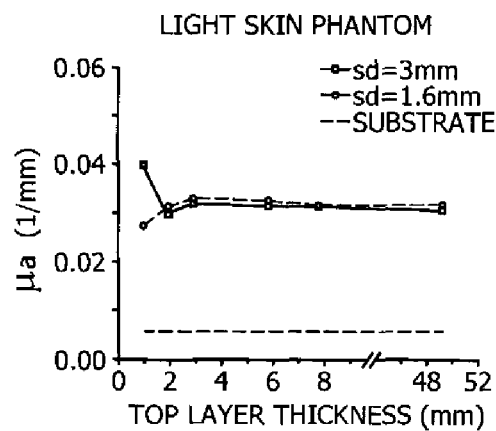
FIGS. 7a and 7b are graphs of the absorption and reduced scattering coefficient recovered from light skin two-layer phantoms.
Figure 7B:
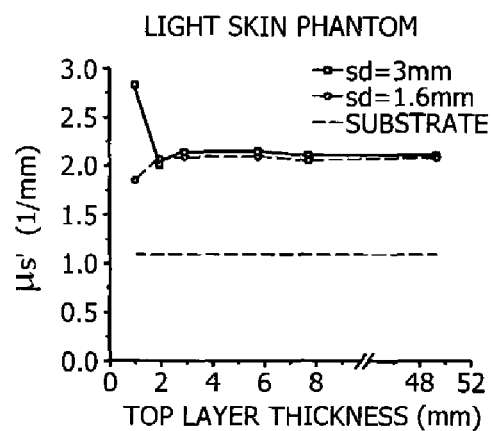
Figure 7C:
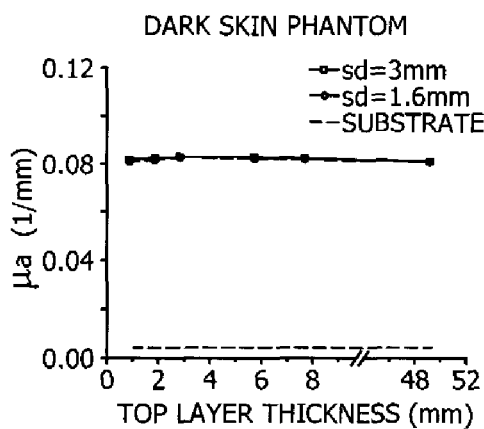
FIGS. 7c and 7d are recovered from dark skin two-layer phantoms. The thickness of the top layer of the two-layer phantoms varies from 1 to 8 mm. Two diffusing probes having source-detector separations of 3 mm (solid squares and solid circles) and 1.6 mm (squares and circles) were employed. Dash-dot lines represent optical properties of the substrate of the two-layer phantoms.
Figure 7D:
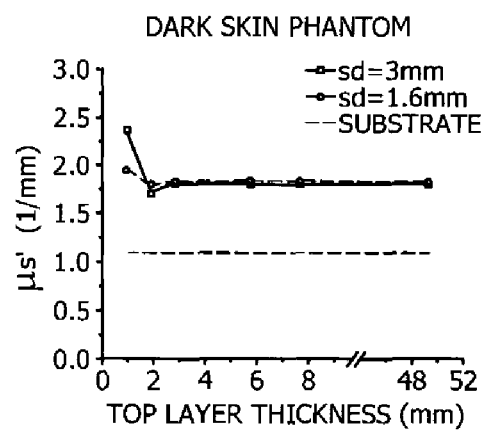

Simulated interrogation depth at the modulation frequency of 50 MHz versus source-detector separations is depicted in FIG. 8, and error bars indicate standard deviations. Increasing the modulation frequency from 50 MHz to 300 MHz can reduce the interrogation depth of the probe. Since the attenuation of the photon density wave is proportional to the modulation frequency, higher modulation frequency photon density waves tend to propagate in the sample in a shorter path length. However, for the parameters employed in the simulations, the variation introduced by changing the modulation frequency is within 3%. Therefore, we present our data only at the modulation frequency of 50 MHz.

Straight lines were fit to the simulated interrogation depths. The trend in interrogation depth versus source-detector separation shown in FIG. 8 indicates that the source-detector separation is proportional to the interrogation depth of a diffusing probe. In FIGS. 7a-7d, we observed that the 1.6-mm source-detector separation diffusing probe can recover more accurate top-layer optical properties than the 3-mm source-detector separation diffusing probe, especially when the top layer of the two-layer phantom is 1 mm thick. The experiment results suggest that the interrogation depth decreases as the source-detector separation decreases. The Monte Carlo simulation results support our experimental observation.

In addition, the slopes of the two fit lines in FIG. 8 indicate that the source-detector separation has a higher impact on the interrogation depth in the light skin samples than in the dark skin samples. By interpolating simulated data shown in FIG. 8, the interrogation depth at 1.6-mm source-detector separation can be estimated to be 1111 m and 865 m for the light skin and dark skin samples, respectively. This decrease in simulated interrogation depth helps to explain the experimental results illustrated in FIGS. 7a-7d. When a 1.6-mm source-detector separation diffusing probe is employed to measure two-layer phantoms having a 1-mm-thick top layer, the deviation of the recovered optical properties from the benchmark values is smaller for the dark skin phantoms than that for the light skin phantoms. On the other hand, although the simulated interrogation depth is 865 m when the dark skin sample is measured with a 1.6-mm source-detector separation diffusing probe, we also observed 4% deviations of recovered optical properties from true values when a dark skin two-layer phantom of a 1-mm-thick top layer was measured with the probe. The deviation may be introduced by the small amount of detected photons that penetrate deeper than the calculated interrogation depth, and could also be a consequence of inherent differences between real experimental measurements and simulations, including probe contact, surface flatness, and the layer structure of real samples.

As illustrated in FIGS. 7a-7d, when the two probes 20 are applied to study the two-layer phantoms with 1-mm top-layer thickness, the recovered optical properties do not always fall in the region between the benchmark optical properties of the top layer and the substrate. In the data recovery, we used the MATLAB "lsqcurvefit" least-squares data-fitting algorithm. The recovered optical properties were obtained using an unconstrained optimization. The recovered unconstrained optical properties and the corresponding values for the two-layer phantoms with a 1-mm-thick top layer are listed in Table II.

|  | 3 mm s-d separation probe | | | | 1.6 mm s-d separation probe | | | |
| --- | --- | --- | --- | --- | --- | --- | --- | --- |
|  | Light Skin Phantom (1 mm) | | Dark Skin Phantom (1 mm) | | Light Skin Phantom (1 mm) | | Dark Skin Phantom (1 mm) | |
|  | unconstrained | constrained | unconstrained | constrained | unconstrained | constrained | unconstrained | constrained |
| Recovered $\mu_a$ (1/mm) | 0.039 | 0.031 | 0.095 | 0.089 | 0.026 | 0.026 | 0.089 | 0.077 |
| Recovered $\mu_s'$ (1/mm) | 2.82 | 1.91 | 2.39 | 1.87 | 1.94 | 1.94 | 2.02 | 1.87 |
| $\chi^2$ | 0.66 | 4.7 | 0.9 | 4.8 | 0.72 | 0.72 | 0.68 | 0.91 |

We also constrained the optimization by requiring that optical properties lie in the range between the benchmark values of the top layer and the substrate. The recovered constrained optical properties and the corresponding values are also found in Table II. From the values shown in Table II, the unconstrained optical properties provide local minima. Based on a comparison of results obtained from constrained versus unconstrained optimizations, we believe that our unconstrained optimization produces optical properties that are not anomalous.

While it seems plausible that recovered optical properties would lie between the extreme values of the optical properties in both layers in this two-layer problem, we are aware of no rigorous argument that establishes this to be the case. To settle this issue would require taking measurements with shorter source-detector separations than can be achieved with our current probe, followed by validation studies such as those presented here. Based on the analysis that we have presented, however, we have no reason to conclude that the optical properties recovered through our unconstrained optimization are spurious.

Farrell et al., investigated the influence of layered tissue structures, such as that found in skin, on tissue optical properties obtained from a diffusion-based model which assumes tissues are semi-infinite and homogeneous. They used multi source-detector separation steady state measurement apparatus and observed that the recovered tissue optical properties were not simply weighted averages of those of individual layers of tissues. Farrell et al., observed nonphysical optical properties when the optimization algorithm was not constrained in the case that the top-layer thickness is smaller than 1.5 mm. In our study, we used two probes which have source-detector separations of 1.6 mm and 3 mm. We can see from FIGS. 7a and 7b that these two probes produce different results when the top-layer thickness is 1 mm. This inconsistency points to a need for additional refinement; in the future, we will investigate further reduction of the source-detector separation and development of a three-layer diffusion model as potential improvements to our approach.

In summary, using our diffusing probes 20, we have characterized two-layer silicone phantoms having various top-layer thicknesses. Measurement results indicate that the recovered top-layer optical properties and deviate from true values within 5% when the top-layer thickness is larger than 2 mm. As the top-layer thicknesses decreases to 1 mm, the deviation of recovered optical properties is strongly dependent on the source-detector separation of the diffusing probe and the optical properties of samples under investigation. Our measurement results indicate that the errors of optical properties recovered from a 1-mm top-layer thickness two-layer phantom are less than 15% when a diffusing probe of 1.6-mm source-detector separation is employed. We observed that interrogation depth decreases as the source-detector separation decreases and as the absorption coefficient of the sample increases. Monte Carlo simulations support our experiment results qualitatively. Simpson et al. indicated the dermis sample they used was from a human abdomen and breast and had a thickness in the range from 1.5 mm to 2 mm. From our measurement and simulation results, it is reasonable to infer that the interrogation region is located primarily in the dermis layer if either the 1.6-mm or 3-mm source-detector separation diffusing probe were employed to measure skin sites at the abdomen and breast. Further reduction in interrogation depth can be achieved by shortening the source-detector separation of the diffusing probe. We can employ our diffusing probe 20 to determine optical properties of in-vivo normal skin and abnormal skin, such as melanoma and port wine stain.

Consider now an embodiment of the invention in the context of chromophore concentrations, absorption and scattering properties of human skin in-vivo. Absorption and reduced scattering coefficients of in-vivo human skin provide critical information on non-invasive skin diagnoses for aesthetic and clinical purposes. To date, very few in-vivo skin optical properties have been reported. In the illustrated embodiment here the probe design was adjusted so that it can use a steady-state white light source alone to determine the spectra of optical properties of skin continuously in the range from 500 to 1000 nm. From the recovered absorption coefficients, the concentrations of chromophores, such as oxyhemoglobin, deoxyhemoglobin, melanin, water, and lipid concentration, in skin can be extracted. It was found that the chromophore concentrations calculated based on the absorption spectra of eighteen subjects at wavelengths above and below 600 nm were distinct because of the inherent difference in interrogation region. The recovered reduced scattering spectra were fit to a scattering power law to obtain the scattering power and intensity. The scattering power, which is related to the average scatterer's size, demonstrates a clear contrast between skin phototypes, skin sites, and wavelengths. We also applied venous occlusion on forearms and found that the concentrations of oxy- and deoxy-hemoglobin as assessed at wavelengths above and below 600 nm were different. Our results suggest that the skin properties determined in the visible and near infrared regions of spectrum with diffuse reflectance techniques derive from skin layers at different depths. Based on our experiment and simulation results, the skin optical properties determined with our diffusing probe were from the upper part (epidermis+papillary dermis) and the lower part of skin (reticular dermis), when the wavelength ranges 500-600 nm and 600-1000 nm were employed, respectively.

In this embodiment, the probe 20 is provided with multiple source-detector pairs so that it can employ a white light source to obtain continuous spectra of absorption and reduced scattering coefficients. The advantages of this multi source-detector separation probe include relative low instrument cost and self-calibration for instrument response (by using the reflectance of one source detection pair as the reference and normalizing the reflectance of other source detector separation pairs to the reference). The normalized reflectance versus source-detector separation is then fit to a diffusion model by a least square minimization algorithm to determine the absorption and reduced scattering spectra. The recovered absorption spectra are fit linearly with known chromophore absorption spectra to extract chromophore concentrations, and the reduced scattering spectra are fit to a scattering power law to obtain the scattering power. The illustrated embodiment of the method uses an internal reference to perform self-calibration to eliminate the influence of the instrument response. The detection fiber 12 penetrates the 1 mm thick Spectralon® layer 14 so that it is flush with the lower surface of the Spectralon® layer 14. There are four source fibers 10a-10d placed on the upper surface of the Spectralon® layer 14 and their distances from the detection fiber 12 are 1.44 mm, 1.92 mm, 2.4 mm, and 2.88 mm, respectively. By using the reflectance from the 1.44 mm source-detector pair as the reference, the reflectance from other source-detector pairs was normalized with respect to the reference reflectance. Thus, a normalized reflectance versus source-detector separation curve can be generated. A modified two-layer diffusion model is employed as a forward model to generate normalized reflectance versus source-detector separation curves to fit the experiment data or measurements obtained from the probe. This self-calibration methodology can be generalized by replacing the distances between the source fibers 10a-10d and the detection fiber 12 mentioned above with arbitrary distance combinations.

The diffusing probe 20 was used to determine the skin optical properties of 18 subjects of different skin phototypes and also extract the chromophore concentrations and the scattering power of skin. It is found that performing the two-regional fitting to the absorption spectrum would result in the best fit with minimal residuals. By two-regional fitting, we mean that absorption coefficient is tit to theory at wavelengths between 500 run and 600 nm and again fit separately between 600 nm and 1000 nm. The rationale for performing the two-regional fitting is that the skin has very different optical properties in the visible and the NIR wavelength regions, and thus the sampling volumes at these two regions are quite different. Monte Carlo simulation results were generated to support this assumption. Likewise, the best fittings for reduced scattering coefficients were obtained when the reduced scattering spectra were fit in the region below and above 600 nm separately. This suggests that the average scatterer sizes determined in the visible and the NIR regions are very different. Results from the measurements carried out here also indicate that the scattering power is not only dependent to anatomical location but also on skin phototype. Finally, experimental results obtained from measuring 10 subjects with forearm venous occlusion were provided. We recovered significantly different hemoglobin concentration at the region below and above 600 nm. Our results agree with those reported by other researchers and support that our proposed probe and fitting method are capable of studying in-vivo superficial tissue at different depths simultaneously.

Figure 9:
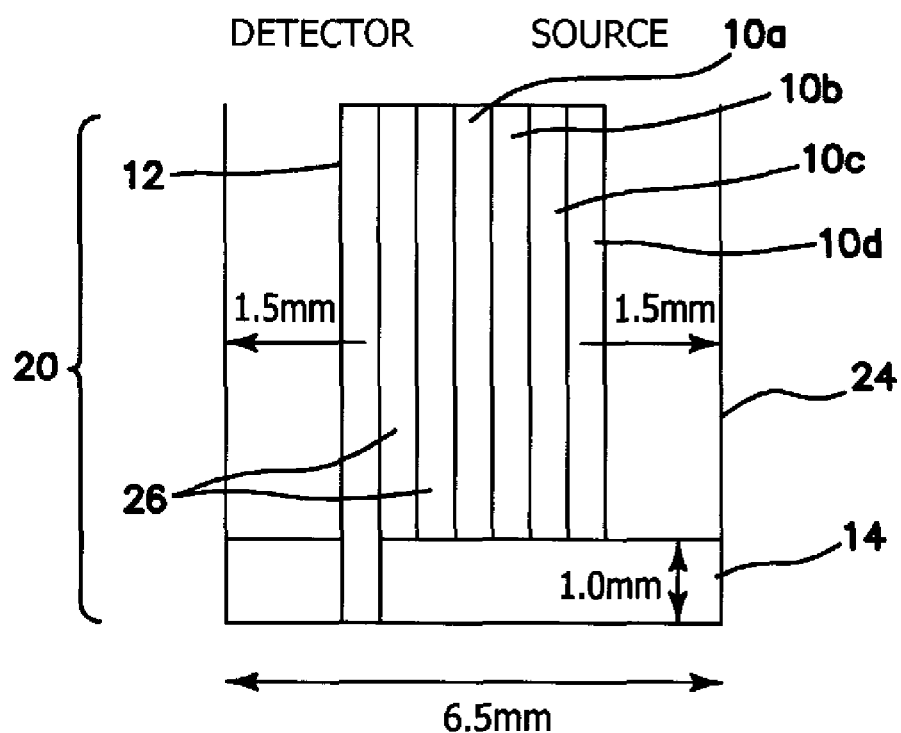
FIG. 9 is a diagram of an embodiment of the probe of the invention wherein multiple source fibers are provided with a single detector fiber and multiple spacer fibers.

The diffusing probe 20 of FIG. 9 used in this embodiment is similar in design to the one described in connection with FIGS. 1b, 2, 3, and 6. The fibers 10a-10d, 12 employed in this probe are 480 μm diameter low OH multimode fibers (core diameter=440 μm) with numerical aperture of 0.22. The diameter of the Spectralon® (Labsphere, NH, USA) disc 14 is 6.5 mm. The detection fiber 12 penetrates the 1 mill thick Spectralon® layer 14 so that it is flush with the lower surface of the Spectralon® layer 14. There are four source fibers 10a-10d placed on the upper surface of the Spectralon® layer 14 and their distances from the detection fiber are 1.44 mm, 1.92 mm, 2.4 mm, and 2.88 mm, respectively. There are two 480 μm spacer fibers 26 placed in between the detection fiber 12 and the first source fiber 10a.

The presence of the detection fiber 12 in the Spectralon® layer 14 disturbs the photon propagation in layer 14 that cannot be properly described by the diffusion theory. This phenomenon is severe when the source is close to the detector. Experimentally, we found that the reflectance measured with the source-detector pair of 0.48 mm and 0.96 mm separation cannot match with the theoretically calculated one. Therefore, in order to make the diffusion model work with our current probe, the shortest source-detector separation was chosen as 1.44 mm.

The detection fiber 12 was connected to a spectrometer equipped with a back-thinned CCD (Model# DTC613, D&W TEK, DE, USA). An I *4 optical switch (Piezosystem jena, MA, USA) was employed to switch between one fiber that is connected to a broadband tungsten halogen light source (not shown) (Model# HL2000, Ocean Optics, FL, USA) and four source fibers 10a-10d of the diffusing probe 20. Because of the limitation imposed by the weak light source intensity below 600 nm, the wavelength range in this study spanned from 500 nm to 1000 nm for subjects with skin type I-IV and spanned from 600 nm to 1000 nm for subjects with skin type V-VI. It is to be expressly understood that other wavelength ranges could be readily accommodated within the scope of the invention.

The optical switch and the spectrometer were connected to a computer and were coordinated and controlled by Labview (National Instruments, TX, USA). At each measurement, four reflectance spectra associated with four source-detector pairs 10a-12, 10b-12, 10c-12, and 10d-12, were sequentially acquired and stored into one tile. The average time required to take one complete measurement is about 10-20 seconds depending on skin pigmentation. By using the reflectance from the 1.44 mm source-detector pair 10a-12 as the reference, the reflectance from other source-detector pairs 10b-12, 10c-12, and 10d-12 were normalized with respect to the reference reflectance. Thus, a normalized reflectance versus source-detector separation curve was generated.

A modified two-layer diffusion model which has been described in detail above was employed as a forward model to generate normalized reflectance versus source-detector separation curves. The curve obtained from the experiment was then fit to the forward model to solve this inverse problem. The "lsqcurvefit" function in MATLAB (MathWorks, MA, USA) was used to perform the least-squares fittings to recover absorption and reduced scattering coefficients. With a personal computer equipped with an Intel Q6600 processor, absorption and reduced scattering spectra from a single sample can be determined within 10 seconds.

Figure 10:
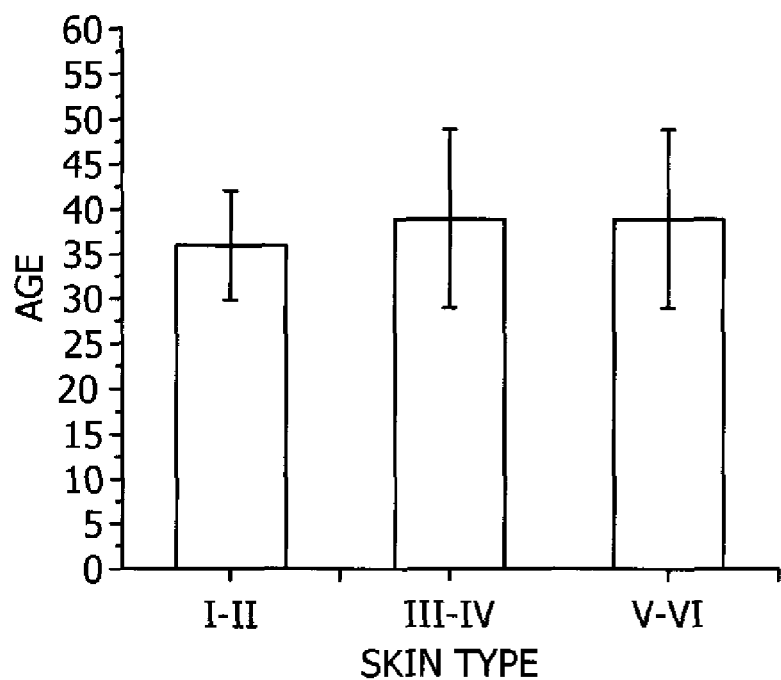
FIG. 10 is a bar graph of the mean and the standard deviation of the age of the subjects in each skin photo-type category used in the study where the probe of FIG. 9 was employed.

Consider now the in-vivo skin measurements which were made. In this study, six subjects in skin type I-II, six subjects in skin type and six subjects in skin type V-VI were recruited. Measurement sites included the dorsal aspect of forearm and the upper inner arm. Three measurements were taken at each anatomic site on each subject, and the probe was physically removed and replaced on each site for each measurement. Because the dorsal forearm is usually a sun-unprotected site while the upper inner arm is relatively a sun-unexposed site we have chosen these locations for the first in-vivo experiments. The mean and the standard deviation of the age of the subjects in each skin photo-type category are shown in FIG. 10. There is no statistically significant difference in age between each group, so that we can rule out the influence of intrinsic ageing on the optical properties when we compare optical properties of different skin type groups.

Consider now the interrogation depth of diffusing probe 20. The diffusing probe 20 was designed to investigate superficial volume of tissues. In order to interpret our results, the interrogation depth of the probe geometry of FIG. 9 needs to be carefully characterized in advance. The details of interrogation depth depend on wavelength dependent optical properties of the sample as well as source-detector separations. Monte Carlo simulations were used to obtain a detailed understanding of the interrogation region and depth of this diffusing probe. Since skin absorption and reduced scattering coefficients at 500 nm are much higher than those at 900 nm, the skin optical properties at 500 nm and 900 nm were used as input parameters in the Monte Carlo simulations. Moreover, the source-detector separations were set to 1.5 mm and 3 mm in the simulations to encompass the range of source-detector separations of our probe. Therefore, four sets (two source-detector distances, two sets of optical properties) of Monte Carlo simulation results will be shown. The Monte Carlo code used here is an extension of the general multi-layer, three dimensional, weighted photon Monte Carlo code.

In order to visualize the distribution of detected photon packets in the superficial diffusing probe geometry, two dimensional fluence distribution maps were generated using Monte Carlo simulations. When a photon packet encounters a collision, a fraction of energy of the photon packet, which is proportional to the weight of the photon packet and the absorption of the medium, is deposited to a local voxel in a three dimensional Cartesian coordinate system. Local fluence (J/mm$^2$) is calculated by dividing the deposited energy by the local absorption coefficient. A three dimensional photon fluence distribution map is obtained by accumulating the fluence distribution of all photon packets arriving at the detector. The three dimensional map is converted to a two dimensional x-z map by binning along the y axis. The maps are normalized by the number of photon packets launched, the volume of a voxel, and the maximal fluence in the map.

In the simulations, we used modified two-layer geometry in which the detection fiber penetrated the top high scattering layer and in contact with the semi-infinite sample layer. The optical properties were set as, $\mu_a=10^{-5}$/mm and, $\mu_s'=50$/mm for the high scattering top layer, and the source-detector separation was 1.5 mm. The indices of refraction of the high scattering layer and the sample were 1.35 and 1.33, respectively. The index of refraction of the source fiber 10a-10d and the detection fiber 12 was not considered in the simulations. The numerical aperture of the fibers 10a-10d, 12 was 0.22. Five million of photon packets were launched in each simulation. To simulate the effect of wavelength dependent optical properties on the size of the interrogation region, we used two sets of optical properties for the sample: $\mu_a=0.05$/mm, $\mu_s'=1.5$/mm to simulate light complexion skin at 900 nm, and $\mu_a=0.11$ mm, $\mu_s'=3$/mm to simulate light complexion skin at 500 nm.

Figure 11A:
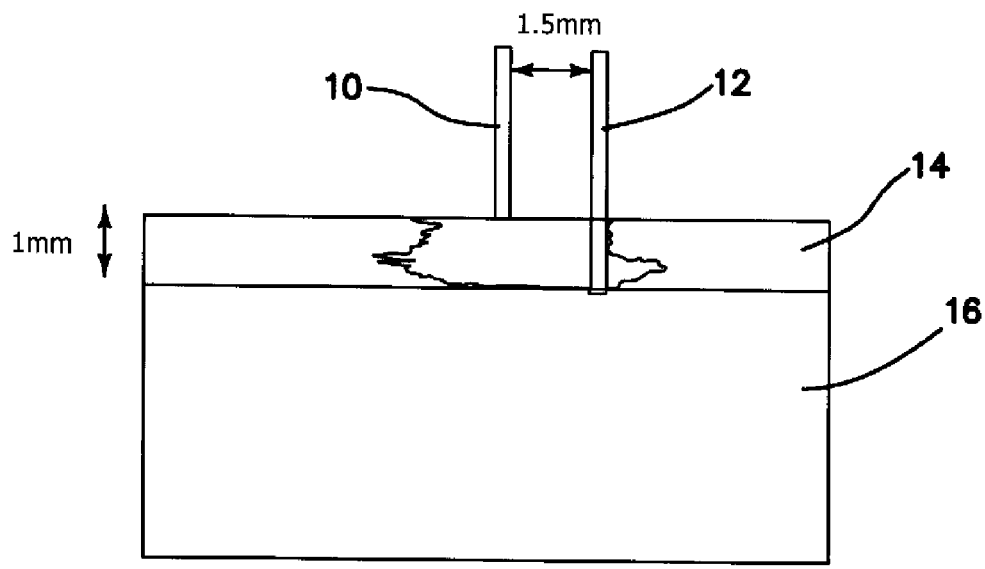
FIG. 11a is a fluence map representing photon distribution in light complexion skin at 500 nm for a diffusing probe with source-detector separation of 1.5 mm.
Figure 11B:
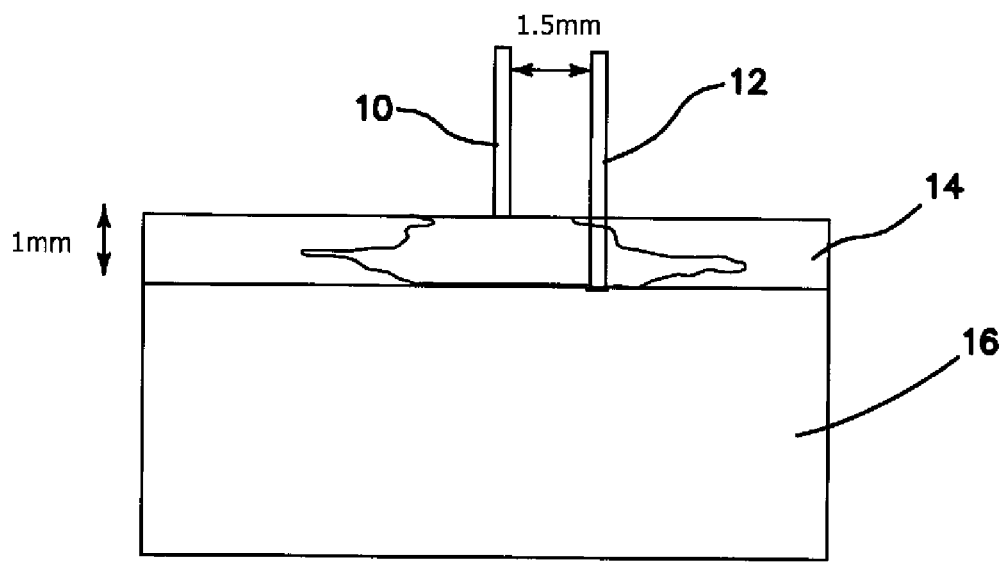
FIG. 11b is a fluence map representing photon distribution in light complexion skin at 900 nm for a diffusing probe with source-detector separation of 1.5 mm.

The distribution maps generated based on these parameters are shown in FIGS. 11a and 11b, where for the sake of simplicity only the source and detector fiber is illustrated, and they are presented here as the logarithm base 10 of the original maps for greater ease of visualization. The fluence map illustrated in FIG. 11a represents photon distribution in light complexion skin at 500 nm and FIG. 11b represents photon distribution in light complexion skin at 900 nm. Comparing FIGS. 11a and 11b qualitatively, it can be seen the "−4" contour line in FIG. 11b is wider and deeper than that in FIG. 11a. This means the diffusing probe has deeper interrogation depths at 900 nm compared to the interrogation depths at 500 nm.

Figure 12A:
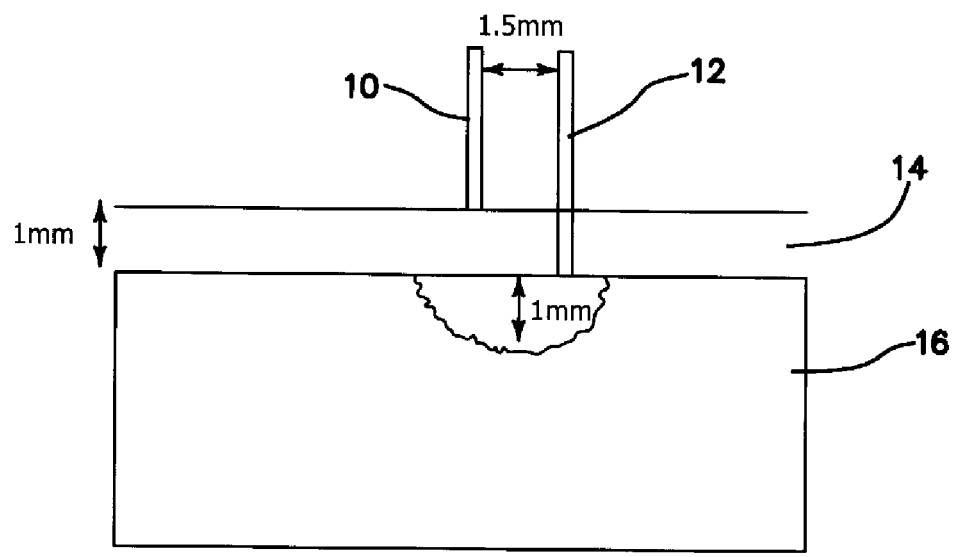
FIGS. 12a and 12b are threshold maps for a diffusing probe with source-detector separation of 1.5 mm where the white area in the threshold maps denotes the voxels that have top 50% 10 greatest fluence values, and black area denotes otherwise.
Figure 12B:
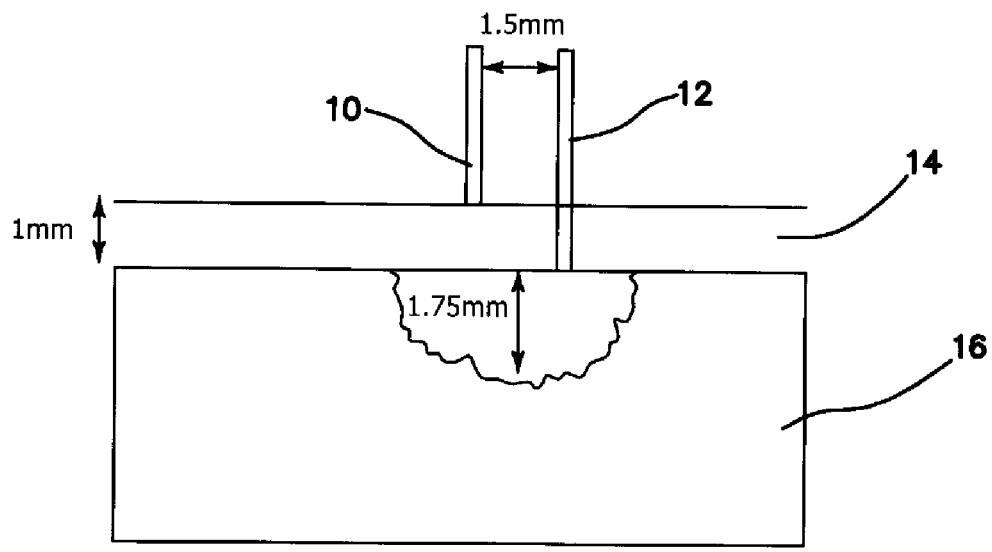

To compare the interrogation depth and region quantitatively, threshold maps were generated, as illustrated in FIGS. 12a and 12b, based on the fluence maps. The threshold maps shown in FIGS. 12a and 12b illustrate only the sample layer and do not include the high scattering layer. The white area in the threshold maps denotes the voxels that have top 50% 10 greatest fluence values, and black area denotes otherwise. The interrogation depth of a 1.5 mm source-detector separation diffusing probe defined by the threshold map shown in FIG. 12a is about 1000 μm at 500 nm while that defined by FIG. 12b is about 1750 μm at 900 nm. The increase in interrogation depth is about 75% as the light source wavelength is changed from 900 nm to 500 nm.

Figure 12C:
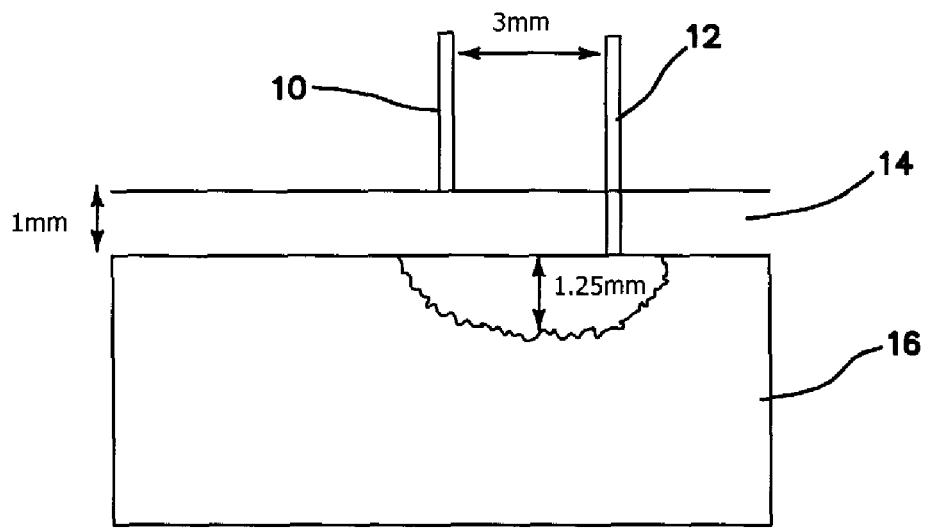
FIGS. 12c and 12d are threshold maps for a diffusing probe with source-detector separation of 3 mm.
Figure 12D:
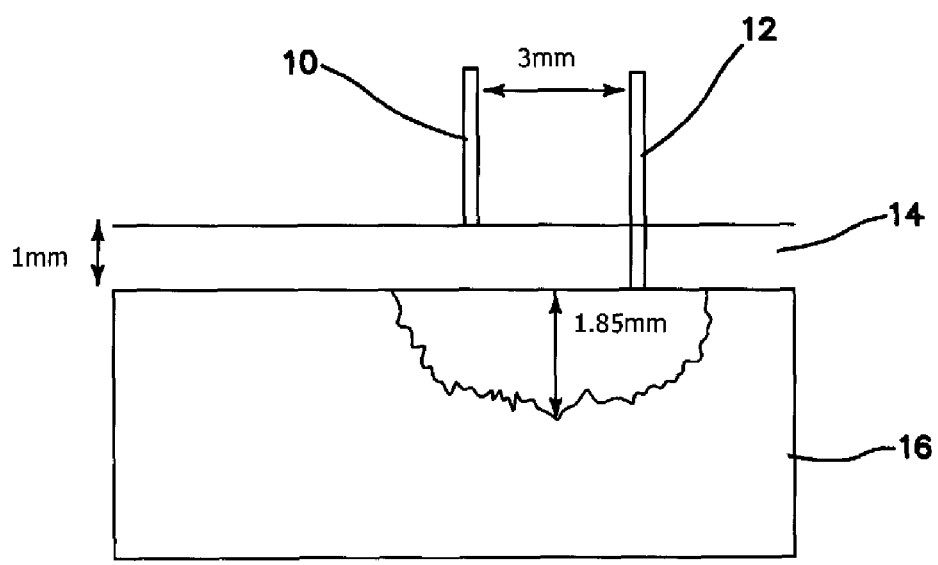

Similarly, the threshold maps were generated for a diffusing probe with source-detector separation of 3 mm and they are illustrated in FIGS. 12c and 12d. The interrogation regions are larger in FIGS. 12c and 12d than in 12a and 12b. The interrogation depths defined by FIGS. 12c and 12d are 1250 μm and 1850 μm, respectively, which represents 48% increase in interrogation depth as the wavelength is changed from 900 nm to 500 nm.

In addition to the interrogation depth defined above, since the Monte Carlo simulations can tally the travel histories of all detected photons, the average interrogation depth of simulation can also be defined as following: Let $$P_i = \frac{w_i}{\sum_{i=1}^{n} w_i}$$

where $W_i$ is the final weight of a detected photon packet and n is the number of photon packets launched. The average interrogation depth of a simulation is determined as $$\bar{z} = \sum_{i=1}^{n} P_i (z_{ave})_i$$

where $$z_{ave} = \sum_{j=1}^{m} d_j / m$$

is the average penetration depth of a detected photon packet, $d_j$ is the depth at which a collision happens in the sample, and m is the total collision number in the sample of the detected photon packet. Based on this definition, the average interrogation depth for the light complexion skin at 500 nm is 646 μm while that for the light complexion skin at 900 nm is 947 μm for the diffusing probe with 1.5 mm source-detector separation. The average interrogation depth is 1100 μm and 1601 μm at wavelengths of 500 nm and 900 nm, respectively, for the diffusing probe with 3 mm source-detector separation. Therefore the average interrogation depth of the diffusing probe has a 45%-47% increase as the light source wavelength is varied from 900 nm to 500 nm. Hence, the interrogation depth and interrogation region are significantly modulated by the light wavelength, whichever definition of interrogation depth is used. The interrogation region of the probe includes epidermis and upper dermis at wavelength of 500 nm. As the wavelength increases to 900 nm, the interrogation region includes epidermis, dermis, and a portion of subcutaneous lipid layer.

Although the detailed results are provided in the related provisional application, Ser. No. 61/140,323, incorporated herein by reference, the optical properties of in-vivo skin of skin types I-VI in the wavelength from 500 nm to 1000 nm are fully characterized using probe 20. Monte Carlo simulations and photon fluence distribution maps described above were generated to characterize the interrogation region of the diffusing probe in typical skin. The results of these simulations indicate that the 24 interrogation depth at 500 nm is at least 46% shallower than that at 900 nm for skin. We can extrapolate this to mean that the skin optical properties obtained with this probe at wavelengths shorter than 600 nm are more relevant to upper dermis and epidermis while those obtained at wavelengths longer than 600 nm are more relevant to dermis. We used the results of these simulations to assist with the analysis of absorption and reduced scattering spectra of in-vivo skin. We performed two-region chromophore fit to the absorption spectra of skin and found that the hemoglobin oxygen saturation was about 60-70% in the upper dermis and about 97-99% in the lower dermis. In addition, the concentration of oxy-hemoglobin in the lower dermis is one order of magnitude higher than that in the upper dermis. Thus the effect of the wavelengths on the interrogation region cannot be overlooked. We also used scattering power law to fit the reduced scattering spectra of dorsal forearm and upper inner arm skin. Our analyses of the scattering power of skin indicates that dorsal forearm skin may have smaller mean scatterer size than upper inner arm skin in the lower dermis. This could be caused by the difference in collagen and elastin bundle size and/or melanin content that are introduced by skin photoaging. On the other hand, the dorsal forearm skin may have larger mean scatterer size than upper inner arm skin in the upper dermis and epidermis, for all skin types. This is possibly the result of different melanin cluster size in the melanosome at different sites. Finally, we demonstrated that our diffusing probe 20 combined with the two-region fitting method were capable of monitoring the variation in hemoglobin concentration of in-vivo skin at different depths simultaneously. We obtained that the deoxy-hemoglobin concentration at upper dermis and oxy-hemoglobin concentration at deeper dermis increased when venous occlusion of 50 mmHg was applied on the forearm. Our results agree with those reported by other researchers and thus further support and validate our proposed method. It is expressly to be understood that the disclosed probe 20 is also capable of characterizing or measuring skin photoaging and in-vivo skin melanin synthesis. The modulation of mean scatterer size as well as chromophore concentrations in the epidermis and dermis introduced by UV radiation is determined using the probe 20.

Figure 2:
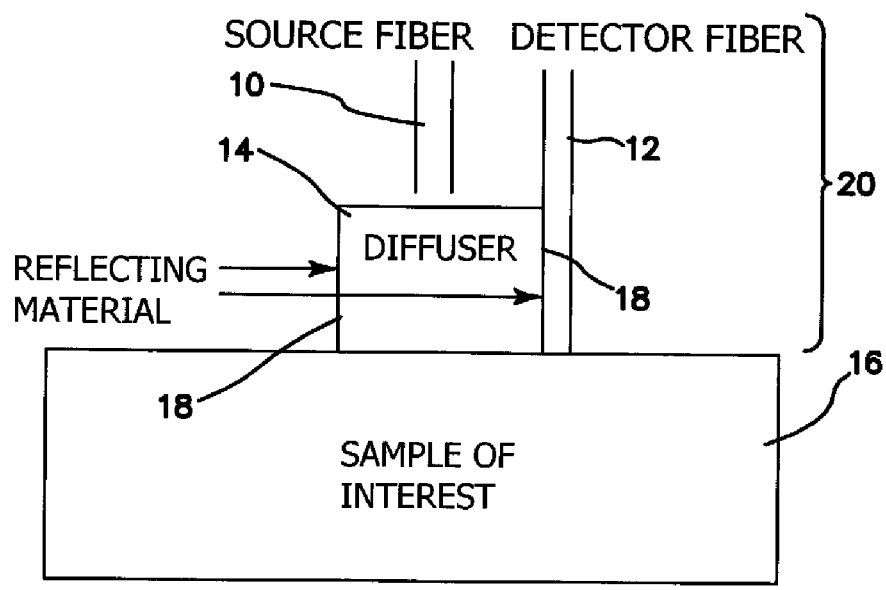
FIG. 2 is a diagram of another embodiment of the invention wherein the diffuser layer is provided with a reflective boundary.
Figure 3:
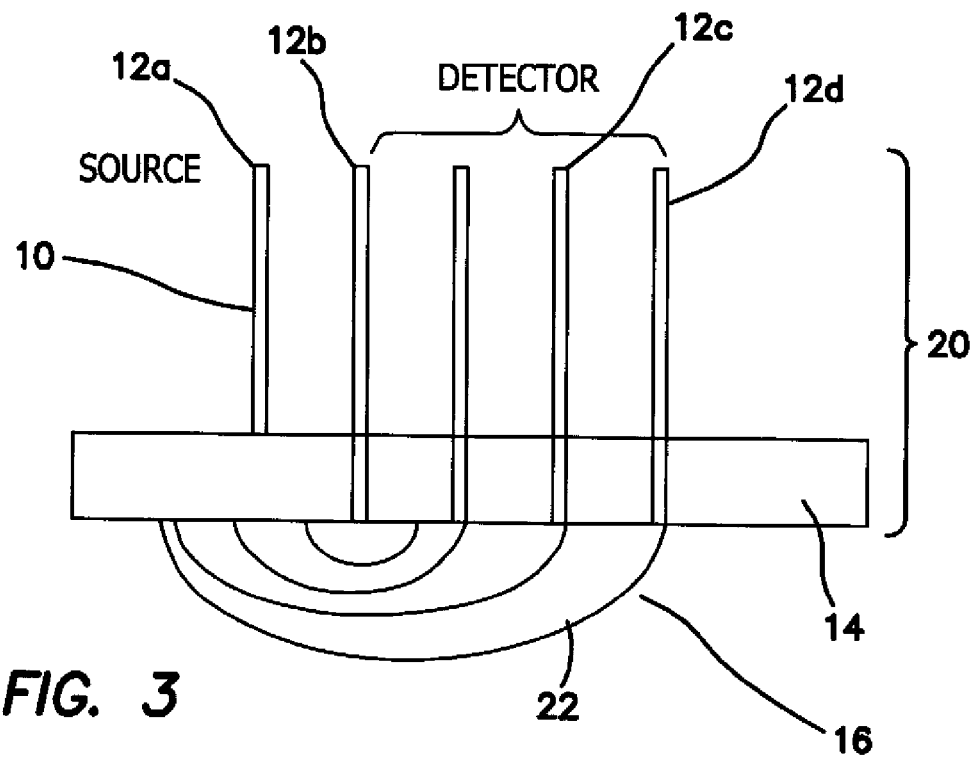
FIG. 3 is a diagram of an embodiment of the invention where a plurality of detector fibers are provided and are disposed through the diffuser layer to enable depth sectioning measurement sensitive to a corresponding different volume of tissue.

Consider now the use of the invention for depth sectioning. The interrogation depth of the probing geometry is proportional to the source-detector separation. Many biological tissues have different properties at different depths, and it is advantageous to quantify optical properties of tissue at various depths. The optical properties obtained using the probe 20 of FIGS. 1b and 2 are the averaged properties of subvolumes that exist in the interrogation region. The shorter the source-detector separation of the probe 20, the greater the contribution of the most superficial volume of the sample to the determined optical properties. When the source-detector separation of the probe 20 is increased, deep tissue volumes contribute more to the recovered optical properties than do the superficial tissue volume. Though the probe 20 cannot determine optical properties of each tissue subvolume exactly, a probe 20 having several source-detector separations can provide the trend of variation in optical properties along the depth. An example of a probe 20 with multiple source-detector pairs 22 is shown in FIG. 3. In the illustrated embodiment a single source 10 is associated with a plurality of detectors 12a-12d, shown here to be four, but the number of detectors is arbitrary. Each detector 12a-12d is disposed through diffuser layer 14 and separated from source 10 by progressive greater distances. Each source-detector pairing provides return signals form a different depth of tissue as symbolically illustrated by the scattering/reflection bands 22 in FIG. 3. Another important feature of a multi source-detector pair probe 20 is that it can be used to recover optical properties of samples 16 without calibration to simplify the measurement procedures.

For applications that include investigation of esophageal and cervical tissues, a probe 20 with a small diameter is essential. Monte Carlo simulations are used to estimate the feasibility of developing an endoscopic probe 20. Monte Carlo simulations carried out which assume that the Spectralon® diffuser layer 14 is a disk shape of finite dimension. The sample 16 under investigation is homogeneous and semi-infinite and has optical properties of $\mu_a=0.03$/mm and $\mu_s'=0.7$/mm which is similar to esophagus. The optical properties of the Spectralon® disk is n=1.35, $\mu_a=10^{-6}$/mm and $\mu_s'=50$/mm. Fifty million photon packets were used for each Monte Carlo simulation. At the lateral boundary of the Spectralon® disk, it is assumed that the Spectralon® disk is surrounded by a perfect absorber, and all photons that reach the boundary will be absorbed. The assumption made here is to consider the feasibility of implementing a proper diffusion model to describe photon propagation in the geometry. All probes require appropriate diffusion models to recover sample optical properties. For an endoscopic probe, the lateral boundary condition has to take into account. Therefore, all parameters, such as the optical properties of the surrounding material, should be describable in the diffusion model. By assuming that the Spectralon® disk is surrounded by a perfect absorber, the property of the surrounding material can be easily defined in a diffusion model (for example, n=1.35, very high absorption, and zero scattering). Alternatively, if the surrounding material is a perfect or partial reflector, its optical properties are difficult to define in the diffusion model.

Figure 4:
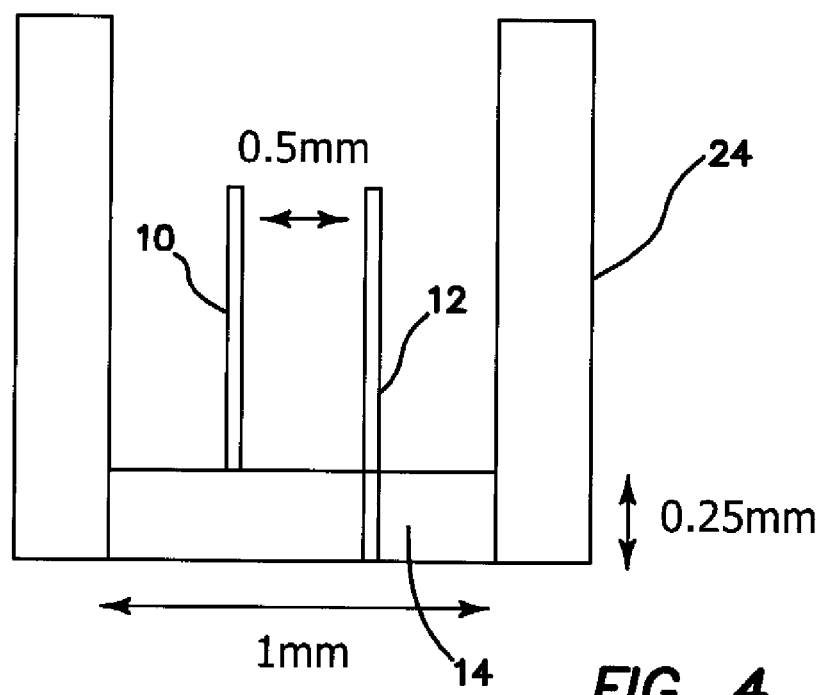
FIG. 4 is a diagram of an embodiment of the invention where the probe is incorporated into an endoscope.
Figure 5A:
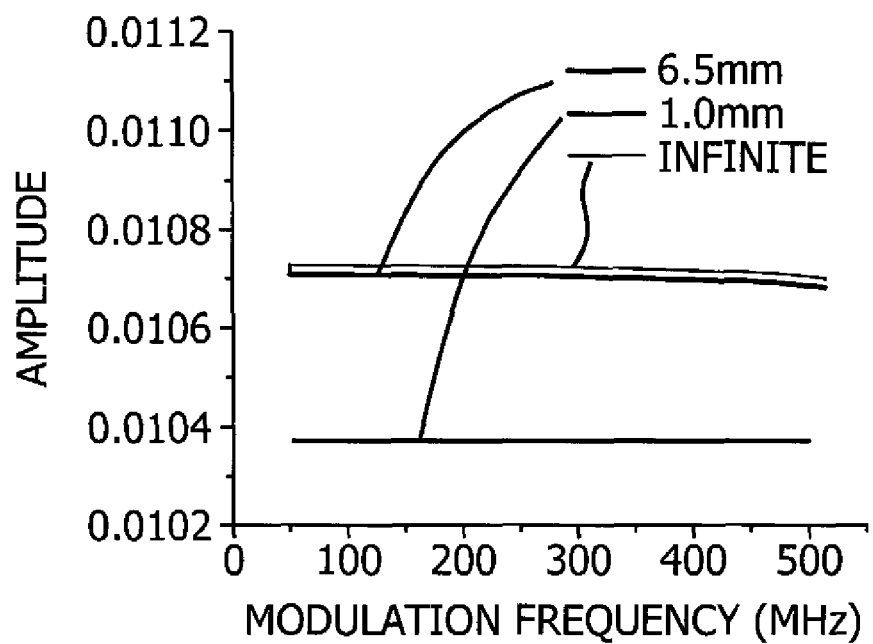
FIG. 5a is a graph of the frequency domain reflectance amplitude and FIG. 5b the phase of three probe geometries. The thinnest lines represent the results of a geometry having the Spectralon® diffuser disk extended infinitely in lateral directions. The thicker lines represent the results of geometries having Spectralon® diffuser disks of diameter of 6.5 mm and 1 mm, respectively. Source-detector separation was set to 0.5 mm in all simulations.
Figure 5B:
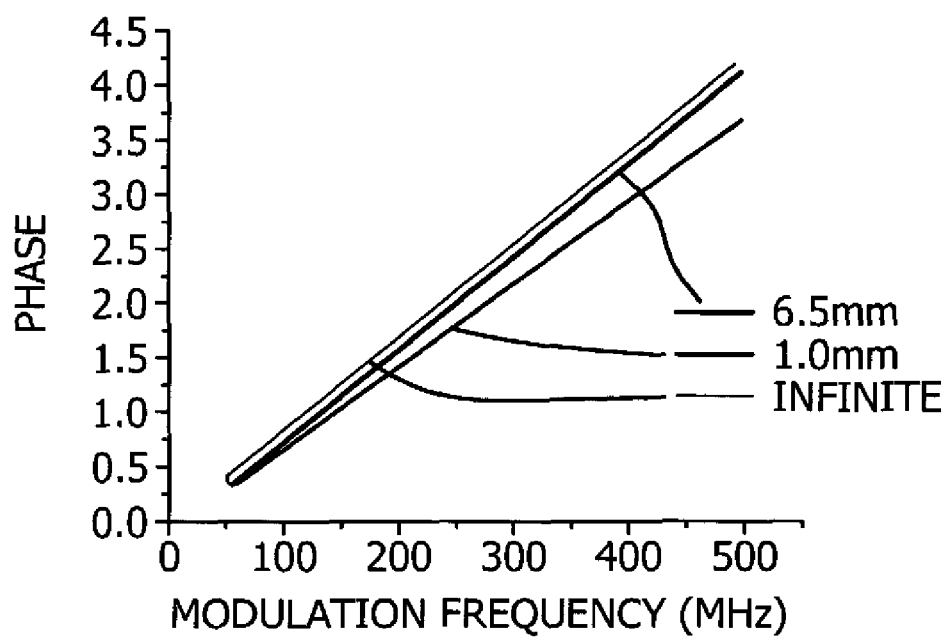

A Monte Carlo simulation was carried out to calculate the reflectance of an endoscopic probe that is depicted in FIG. 4. The endoscope is shown as a cylindrical catheter 24, the distal tip of which is shown in FIG. 4 and is provided with an end window comprised of diffuser layer 14, a fiber source 10 and a fiber detector 12 disposed through diffuser layer 14 as in the embodiment of FIG. 1b with the addition of being surrounded by a catheter wall 24 treated as a perfect absorber. The diameter of the Spectralon® disk or diffuser layer 14 was 1 mm in the simulation. The thickness of the Spectralon® slab and the source-detector separation were 0.25 mm and 0.5 mm, respectively. Source-detector separation of an endoscope probe should not be larger than 1-2 mm, since the diameters of conventional endoscope probes are generally in the range of 1 mm to 3 mm. However, source-detector separation to Spectralon® thickness ratios different from the value illustrated here are expressly contemplated. The phase and amplitude responses of this probe are shown in FIGS. 5a and 5b respectively as a function of modulation frequency.

Next, two additional Monte Carlo simulations were carried out to study the effect of the lateral dimension of Spectralon® diffuser disk 14 on the measured reflectance. The thickest lines in FIGS. 5a and 5b illustrate Monte Carlo simulated amplitude and phase responses obtained using a probe that used a Spectralon® slab with diameter of 6.5 mm. The diameter of Spectralon® diffuser disk 14 selected here is comparable to that of a clinical probe. The thickness of the Spectralon® diffuser disk 14 and the source-detector separation were set as 0.25 mm and 0.5 mm, respectively. The lines of thinnest thickness in FIGS. 5a and 5b illustrate the phase and amplitude response generated for a geometry that uses an infinitely wide Spectralon® diffuser disk 14 with a thickness of 0.25 mm and a source-detector separation of 0.5 mm. It can be seen that the phase and amplitude responses illustrated in lines representative of a 6.5 mm and infinite diameter diffuser disk 14 are almost indistinguishable. Therefore, the detected reflectance in the geometry that uses a Spectralon® diffuser disk 14 of diameter 6.5 mm is not affected by the lateral boundaries of the Spectralon® diffuser disk 14. On the other hand, the lines in FIGS. 5a and 5b, which represent the reflectance of an endoscopic probe with Spectralon® diffuser disk 14 diameter of 1 mm, deviate from the other lines materially. This deviation results from the change in lateral boundary conditions. As the disk diameter is decreased to 1 mm, the lateral boundary is not negligible and the reflectance cannot be predicted precisely by a modified two layer diffusion model which assumes the Spectralon® diffuser disk 14 has infinite extent in lateral directions. To account for the lateral boundary conditions for an endoscopic probe, an improved diffusion model is necessary. Several researchers have proposed solutions for the diffusion equation in a layered medium that has finite dimension in lateral and axial directions. Others have used an eigenfunction method to solve the diffusion equation for a two- or three-layered finite diffusive medium, which considered lateral and axial boundaries. Still others derived the solution of the diffusion equation for a turbid (rectangular) parallelepiped using the method of image sources and applying extrapolated boundary conditions. The models mentioned above may be employed to correctly calculate reflectance detected by an endoscopic probe.

a. Theoretically, the MTL diffusion model used in the illustrated embodiment is valid as long as average sample $\mu'_s$ is larger than $\mu_a$. For tissues having absorption coefficients higher than their reduced scattering coefficients, the MTL diffusion model is no longer valid. An improved theoretical model, such as $\delta$-$P_1$ diffusion model, is necessary for measuring tissues having absorption coefficients higher than their reduced scattering coefficients. It has been demonstrated that the $\delta$-$P_1$ diffusion model can be used to determine optical properties of samples having arbitrary albedo (albedo=$\mu_s'/(\mu_s'+\mu_a)$). The magnitude of the skin absorption coefficient is comparable to that of the skin reduced scattering coefficient in the visible and mid-infrared range. In the visible and mid-infrared range, the diffusion approximation for the standard diffusion equation is no longer valid. Therefore, as the operating wavelength range shifts to visible or mid-infrared for clinical applications such as melanoma and skin hydration, it is crucial to employ a diffusion model like the $\delta$-$P_1$ diffusion model, which is applicable to sample having arbitrary albedo, to ensure the recovered optical properties are accurate. Moreover, since the current MTL diffusion model assumes that the sample under investigation is semi-infinite and homogeneous, the recovered optical properties represent the average of optical properties of whole interrogation volume. By incorporating a multi-layer diffusion model, such as three-layer or four-layer diffusion model, with the probe, it is possible to recover sample optical properties at various layers.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A probe for obtaining quantitative optical properties and chromophore concentrations of tissue components in tissue in-vivo at superficial depths and at source-detector separations of 5 mm or less comprising:
   a source fiber providing light to expose the tissue;
   a diffuser layer into which light from the source fiber is directed and then from the diffuser layer to and/or into the tissue,
   a detector fiber arranged relative to the diffuser layer for detecting backscattered and/or reflected light returned from the tissue without transmission through the diffuser layer; and
   a processor circuit including a spectrometer optically coupled to the detector fiber for analyzing the backscattered and/or reflected light from the tissue to determine the quantitative optical properties and chromophore concentrations of tissue components.

2. The probe of claim 1 further comprising a light source optically coupled to the source fiber.

3. The probe of claim 1 where the detector fiber is disposed through the diffuser layer.

4. A probe for obtaining quantitative optical properties and chromophore concentrations of tissue components in tissue in-vivo at superficial depths and at source-detector separations of 5 mm or less comprising:
   a source fiber providing light to expose the tissue;
   a diffuser layer into which light from the source fiber is directed and then from the diffuser layer to and/or into the tissue; and
   a detector fiber arranged relative to the diffuser layer for detecting backscattered and/or reflected light returned from the tissue without transmission through the diffuser layer,
   where the diffuser layer is composed of Spectralon®.

5. A probe for obtaining quantitative optical properties and chromophore concentrations of tissue components in tissue in-vivo at superficial depths and at source-detector separations of 5 mm or less comprising:
   a source fiber providing light to expose the tissue;
   a diffuser layer into which light from the source fiber is directed and then from the diffuser layer to and/or into the tissue; and
   a detector fiber arranged relative to the diffuser layer for detecting backscattered and/or reflected light returned from the tissue without transmission through the diffuser layer,
   where the diffuser layer has an absorption coefficient of less than or equal to approximately $\mu_a=10^{-6}$/mm and a reduced scattering coefficient equal or greater than $\mu_s=35$/mm.

6. A probe for obtaining quantitative optical properties and chromophore concentrations of tissue components in tissue in-vivo at superficial depths and at source-detector separations of 5 mm or less comprising:
   a source fiber providing light to expose the tissue;
   a diffuser layer into which light from the source fiber is directed and then from the diffuser layer to and/or into the tissue;
   a detector fiber arranged relative to the diffuser layer for detecting backscattered and/or reflected light returned from the tissue without transmission through the diffuser layer; and
   an endoscope with a distal end and a lateral boundary at the distal end, the probe being provided at or near the distal end of the endoscope as an endoscopic window, the diffuser layer having a minimum width greater than 1 mm so that the lateral boundary of the endoscope does not substantially affect probe measurements.

7. The probe of claim 6 where the minimum width of he diffuser layer is 6.5 mm or greater.

8. The probe of claim 6 where the detector fiber and source fiber are separated by approximately 3 mm or less.

9. A probe for obtaining quantitative optical properties and chromophore concentrations of tissue components in tissue in-vivo at superficial depths and at source-detector separations of 5 mm or less comprising:
   a source fiber providing light to expose the tissue;
   a diffuser layer into which light from the source fiber is directed and then from the diffuser layer to and/or into the tissue
   a detector fiber arranged relative to the diffuser layer for detecting backscattered and/or reflected light returned from the tissue without transmission through the diffuser layer; and
   a plurality of source fibers, each source fiber having a different distance from the detector fiber so that each source-detector fiber pair provides a depth sectioning measurement sensitive to a corresponding different volume of tissue.

10. The probe of claim 9 where the plurality of source fibers are each spaced from each other.

11. The probe of claim 10 where the plurality of detector fibers are each spaced from each other.

12. The probe of claim 10 where the plurality of detector fibers are each adjacent to each other.

13. The probe of claim 9 where the plurality of source fibers are each adjacent to each other.

14. A probe for obtaining quantitative optical properties and chromophore concentrations of tissue components in tissue in-vivo at superficial depths and at source-detector separations of 5 mm or less comprising:
   a source fiber providing light to expose the tissue;
   a diffuser layer into which light from the source fiber is directed and then from the diffuser layer to and/or into the tissue;
   a detector fiber arranged relative to the diffuser layer for detecting backscattered and/or reflected light returned from the tissue without transmission through the diffuser layer; and
   a plurality of detector fibers, each detector fiber having a different distance from the source fiber so that each source-detector fiber pair provides a depth sectioning measurement sensitive to a corresponding different volume of tissue.

15. A probe for obtaining quantitative optical properties and chromophore concentrations of tissue components in tissue in-vivo at superficial depths and at source-detector separations of 5 mm or less comprising:
   a source fiber providing light to expose the tissue:
   a diffuser layer into which light from the source fiber is directed and then from the diffuser layer to and/or into the tissue;
   a detector fiber arranged relative to the diffuser layer for detecting backscattered and/or reflected light returned from the tissue without transmission through the diffuser layer; and
   at least one spacer fiber and where the source, detector and spacer fibers are bundled together to form an adjacent collection of fibers.

16. A probe for obtaining quantitative optical properties and chromophore concentrations of tissue components in tissue in-vivo at superficial depths and at source-detector separations of 5 mm or less comprising:
   a source fiber providing light to expose the tissue;
   a diffuser layer into which light from the source fiber is directed and then from the diffuser layer to and/or into the tissue,
   a detector fiber arranged relative to the diffuser layer for detecting backscattered and/or reflected light returned from the tissue without transmission through the diffuser layer; and
   a plurality of spacer fibers and a plurality of detector fibers arranged and configured with the source fiber to form a compact bundler of fibers with a plurality of spacing between the source fiber and each of the plurality of detector fibers, so that each source-detector fiber pair provides a depth sectioning measurement sensitive to a corresponding different volume of tissue.

17. A probe for obtaining quantitative optical properties and chromophore concentrations of tissue components in tissue in-vivo at superficial depths and at source-detector separations of 5 mm or less comprising:
 a source fiber providing light to expose the tissue;
 a diffuser layer into which light from the source fiber directed and then he diffuser layer to and/or into the tissue; and
 a detector fiber arranged relative to the diffuser layer for detecting backscattered and/or reflected light returned from the tissue without transmission through the diffuser layer,
 where the source and detector fibers have a distal planar area and where the diffuser layer has a side boundary and a planar area of the same order of magnitude at the distal planar area of the source and detector fibers themselves and where the side boundary of diffuser layer is provided with a reflective material.

18. A probe for obtaining quantitative optical properties and chromophore concentrations of tissue components in tissue in-vivo at superficial depths and at source-detector separations of 5 mm or less comprising:
 a source fiber providing light to expose the tissue;
 a diffuser layer into which light from the source fiber is directed and then from the diffuser layer to and/or into the tissue; and
 a detector fiber arranged relative to the diffuser layer for detecting backscattered and/or reflected light returned from the tissue without transmission through the diffuser layer,
 where the diffuser layer, source and detector fibers are characterized by a maximum width having a magnitude less than a hollow core needle employed for breast cancer biopsy or for transurethral delivery to the prostate or bladder.

19. A method for self-calibrating a tissue probe having a plurality of source-detector pairs with a corresponding plurality of source-detector separation distances in which probe light from the source corresponding to each source-detector pair is transmitted through a diffuser layer, and in which probe each detector corresponding to each source-detector pair receives light from the tissue without transmission through the diffuser layer, the method comprising:
 selecting and measuring one of the plurality of source-detector pairs as a reference reflectance measurement;
 measuring and normalizing the reflectances from the remaining other ones of the plurality of source-detector pairs; and
 generating a corresponding plurality of normalized reflectance versus source-detector separation curves to fit the measurements obtained from the plurality of source-detector pairs included in the probe.

* * * * *